United States Patent [19]
Salter

[11] Patent Number: 5,342,190
[45] Date of Patent: Aug. 30, 1994

[54] APPARATUS FOR EMPLACING VISCOUS MATERIAL IN A CAVITY

[75] Inventor: James R. Salter, The Woodlands, Tex.

[73] Assignee: Optex Biomedical, Inc., The Woodlands, Tex.

[21] Appl. No.: 918,651

[22] Filed: Jul. 22, 1992

[51] Int. Cl.⁵ ............................................. B29C 31/06
[52] U.S. Cl. ................................... 425/469; 422/58; 422/63; 422/100
[58] Field of Search .................. 425/469, 129.1, 376.1; 422/58, 63, 100, 102, 104

[56] References Cited

U.S. PATENT DOCUMENTS

| | | | |
|---|---|---|---|
| 4,682,895 | 7/1987 | Costello | 356/402 |
| 4,781,567 | 11/1988 | Miller, Jr. | 425/469 X |
| 4,830,832 | 5/1989 | Arpagaus et al. | 422/63 X |
| 4,889,407 | 12/1989 | Markle et al. | 356/39 X |
| 4,927,765 | 5/1990 | Saxon et al. | 422/63 X |
| 4,980,130 | 12/1990 | Metzger et al. | 422/63 X |
| 4,994,240 | 2/1991 | Hayashi | 422/63 |
| 4,999,306 | 3/1991 | Yafuso et al. | 436/68 |
| 5,054,882 | 10/1991 | Riccitelli et al. | 385/12 |
| 5,124,130 | 6/1992 | Costello et al. | 422/82.06 |
| 5,158,748 | 10/1992 | Obi et al. | 422/63 X |
| 5,179,024 | 1/1993 | Dahms | 422/58 X |

Primary Examiner—Richard L. Chiesa
Attorney, Agent, or Firm—Guy McClung

[57] ABSTRACT

Apparatus are disclosed for introducing thick material into a small cavity, the apparatus in one aspect including a piston/cylinder device insertable into a block bore of a containment block, the block bore having the thick material therein for transfer to the piston bore, the piston then movable to expel the material from the piston bore into the cavity; in certain aspects the cavity of microscopic size and in other aspects thick material being a thixotropic chemical indicating material and the cavity extending through a fiber optic in a biosensor;

9 Claims, 3 Drawing Sheets

APPARATUS FOR EMPLACING VISCOUS MATERIAL IN A CAVITY

BACKGROUND OF THE INVENTION

1. Field Of The Invention

This invention is directed to: devices and procedures for emplacing thick viscous materials in a cavity; in one aspect, to such devices and procedures for emplacing a thixotropic material in a microscopic cavity; and in one specific aspect to such devices and methods for emplacing a chemical indicator in a biosensor.

2. Description Of Related Art

Difficulties are encountered in inserting a viscous material into a small cavity or hole. As a wet media is initially introduced into such a cavity, it can effectively seal off an opening into the cavity and trap therein any air in the cavity. Entrapped air can prevent total filling of a cavity and can also become interspersed within the material inserted into the cavity, adversely affecting the material or its performance and degrading certain desired properties (e.g. physical, optical, or chemical) of the material. Other difficulties are encountered when a very small amount (e.g. several nanoliters) of a thick material is to be inserted into a cavity of microscopic dimensions, especially when the amount of the material is critical. Pumping thick viscous material with a conventional syringe or through a conventional pipette has proven to be unsatisfactory.

In one particular technology, the manufacturing of a fiber optic biosensor having a microscopic sized cavity filled with an optical chemical indicator complex, the chemical indicator complex may consist of a solid and liquid matrix of extremely high viscosity, forming a thixotropic paste. In certain embodiments the solid component is a closely packed mass of microscopic particles such as porous ground glass, or plastic microspheres. These solids are the substrate to which the chemical indicator is bonded for immobilization. The liquid component is a viscous polymer water gel or a viscous silicone oil, serving as an ion transport media, a gas transport media for optical coupling media, and an adhesive media for physical integrity. The solids and liquid are mixed in a critical ratio such that the solids are closely packed to the highest possible density, with only enough liquid to fill the interstitial spaces between particles. The chemical indicator cavity in the fiber optic biosensor is a container that holds part of the chemical indicator complex in the optical path of fiber light conductors. The cavity may be as small as 100 microns long, wide, and deep. The cavity is open on one side so that the chemical indicator complex may be installed. The cavity is sealed by covering the opening with a polymer layer. The various difficulties mentioned above have been encountered in attempts to effectively and efficiently insert such a chemical indicator complex into a sensor's cavities.

There has been a need for an effective device and method for emplacing a desired amount of a thick material into a small cavity. There is a need for such devices and methods for introducing a very small amount of a thixotropic material into a microscopic cavity. There is a need for such devices and methods for inserting a known very small amount of a chemical indicator into a microscopic cavity in a fiber optic biosensor.

SUMMARY OF PRESENT INVENTION

The present invention discloses apparatuses and related methods for accurately emplacing thick material in a small cavity. Thick materials include, but are not limited to clay, asphalt, putty, paste, suspension, peanut butter, fudge, and biosensor chemical indicators; although these materials are not equivalents of each other. In one embodiment the apparatus has a piston/cylinder with a movable piston disposed in a piston bore therein. Preferably, there is not an air tight fit between the piston and the piston bore so that air in the piston bore can escape. The piston/cylinder combination is insertable into a containment block having a block bore which contains the thick material to be inserted into a cavity. The cylinder-piston combination is inserted into the block bore with the piston withdrawn in the cylinder so that some of the thick material enters the piston bore. The block bore's interior surface eliminates alternate flow paths for the thick material other than into the piston bore. By appropriate sizing and configuration of the various parts and bores, a known amount of the thick material enters the piston bore. The cylinder-piston combination is removed from the containment block with the desired amount of thick material in the piston bore. The cylinder-piston combination is then held at an opening of a small cavity and the piston is pushed thereby moving the thick material from the piston bore into the small cavity. The block bore can be a hole through a block which initially is not closed off. Filling the bore with thick material through one end pushes air out the other end. A movable block is then held or clamped at one end of the block bore while the cylinder/piston combination is inserted in the other end of the block bore. Preferably the movable block is not air tightly sealed against the containment block. In one embodiment a containment block has a base with a guide groove in it to receive and hold a base of a piston cylinder subassembly.

In one specific embodiment a known amount of thixotropic chemical indicator complex is introduced into a microscopic cavity in a biosensor, e.g. a biosensor in which the cavity or cavities are in a fiber optic. A quantity of indicator complex is manually (or mechanically) pressed into a block bore, open at both ends, then one end is blocked by a plane surface, leaving the other end open. A piston/cylinder with a piston bore is then pressed into the open end of the block bore, so that the indicator complex is transferred into the bore of the piston/cylinder. The outside diameter of the piston's cylinder is, preferably, a close fit to the inside diameter of the block bore. The piston is withdrawn within its bore, leaving a space within (preferably of known desired volume or of known excess volume), to receive the indicator complex. The piston and cylinder are positioned such that the opening of the cylinder is adjacent to the opening of the cavity in the fiber biosensor. Next, the indicator complex is pushed out of the cylinder by movement of the piston. The indicator complex enters the cavity as a slug of thixotropic material, which proceeds to the bottom of the cavity. Air in the cavity is vented via an exit path for the air above the slug of material, since the slug of indicator is smaller in width than the cavity width until it reaches the bottom of the cavity. Then the slug flows transversely, and conforms to the dimensions of the cavity, from the bottom upward, in an advancing front of continuous material. When the cavity is full, the piston is stopped, and the filling is complete, with little or no air inclusion. In one particular preferred embodiment the cavity is cubical, 100 microns in length on a side with one side open; the cylinder has an inside diameter of 100 microns and an outside diameter of 500 microns; and the block bore has an inside diameter of 500 microns.

This two stage process for filling a cavity includes, in at least certain preferred embodiments: pressing material into a relatively large block bore, and then transferring it into the smaller piston bore. This is due, in certain preferred embodiments, to the fact that the outside diameter of the piston cylinder seals (by close fit) against the inside diameter of the packing bore. The operation is also made practical because the axial depth of the block bore and the length of the slug of material are relatively short compared with other conventional means. This axial depth may, in certain preferred embodiments, be equal to about five piston diameters.

The extreme pressures needed to move thick materials with certain prior art devices are not required by certain embodiments of the present invention; hence the mixture separation (e.g. liquid from solid) encountered at these high pressures does not occur with these embodiments; i.e., material integrity is preserved.

It is, therefore, an object of at least certain preferred embodiments of the present invention to provide:

New, useful, unique, efficient, and effective devices and methods for introducing thick material into a small cavity or hole;

Such devices and methods for inserting thixotropic materials, including but not limited to chemical sensor indicators, into small cavities;

Such methods and devices for use in emplacing such materials in cavities of microscopic size;

Such methods and devices for use in emplacing such materials in microscopic cavities in sensors which use fiber optics;

Such devices and methods which are useful in emplacing a known and very small amount of such materials in such cavities;

Such devices and methods for filling such cavities with such materials;

Such devices and methods which accomplish material emplacement while reducing or eliminating the trapping of undesirable material (e.g. but not limited to air or water) in a cavity while it is being filled, and Such devices and methods which accomplish the movement of thick materials while preserving the material's integrity, particularly the integrity and composition of mixtures, especially liquid/solid mixtures.

The present invention recognizes and addresses the previously-mentioned problems and needs and provides a solution to those problems and a satisfactory meeting of those needs in its various possible embodiments and equivalents thereof. To one of skill in this art who has the benefits of this invention's realizations, teachings and disclosures, other and further objects and advantages will be clear, as well as others inherent therein, form the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention as broadly as legally permissible no matter how others may later disguise it by variations in form or additions of further improvements.

BRIEF DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate certain preferred embodiments of the invention and are therefore not to be considered limiting of its scope, for the invention may admit to other equally effective equivalent embodiments.

DESCRIPTION OF PREFERRED EMBODIMENTS

Figure 1:
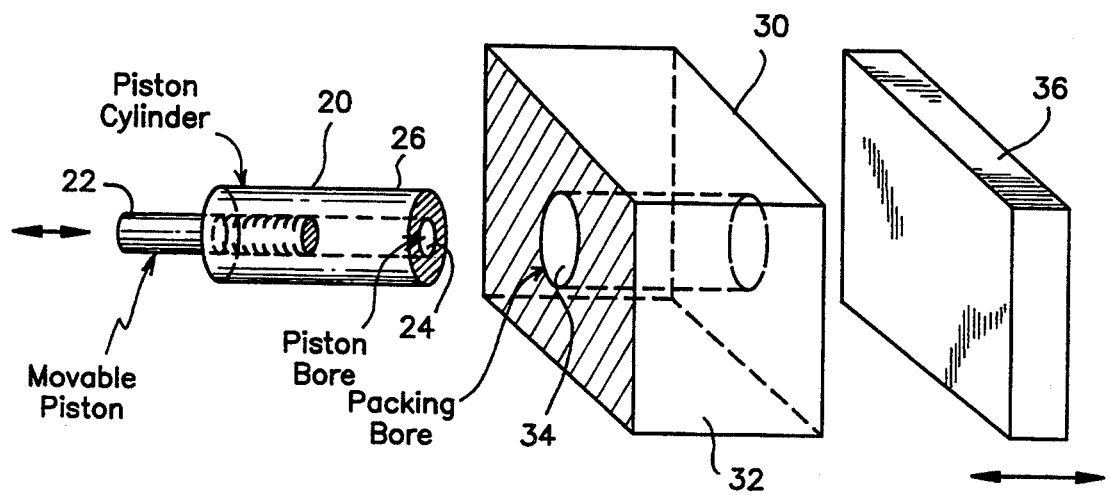
FIG. 1 is a schematic side view of an assembly according to the present invention.

Referring now to FIG. 1, a material handling assembly 10 according to the present invention includes a piston/cylinder sub-assembly 20 and a containment block sub-assembly 30. The piston/cylinder sub assembly 20 has a piston 22 movably disposed in a piston bore 24 in a cylinder 26. Preferably the parts of the piston/cylinder sub-assembly 20 and the piston bore 24 are sized and configured so that movement of the piston 22 a known distance out of the piston bore 24 creates a space within the piston bore 24 of known desired volume so that when the bore is filled with thick material it is of a desired volume for insertion into a cavity of known volume to fill the cavity efficiently and without waste or excess material. The containment sub-assembly 30 has a containment block 32 with a block bore 34 therein for holding the thick material. Thick material is placed in the block bore 34, e.g. manually with the aid of a spatula. A movable sub-block 36 is used to block the thick material in the block bore 34 and to insure that the block bore 34 is full of material. Also, having such a movable block facilitates cleaning out of the blockbore, particularly if the thick material has hardened or if it has thickened further.

Preferably there is no air tight seal between the sub-block 36 and the containment block 32 so that air is not entrapped in the block bore 34., i.e., an escape path is provided for air. In certain preferred embodiments the block bore has an axial depth equal to or less than about five times the diameter of the piston.

Figure 2:
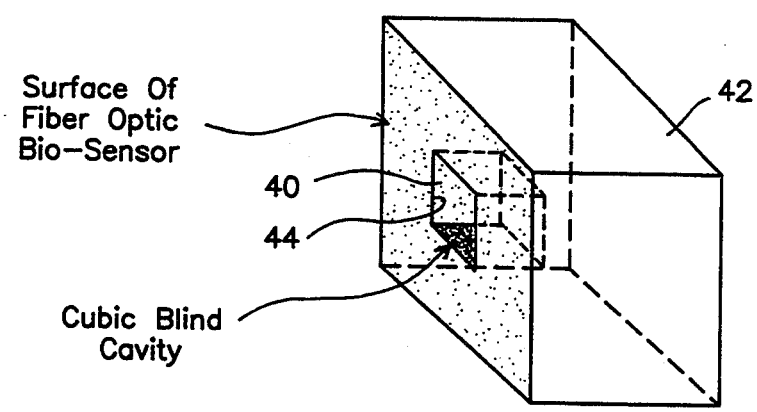
FIG. 2 is a schematic perspective view of a cavity into which material is to be introduced.
Figure 3:
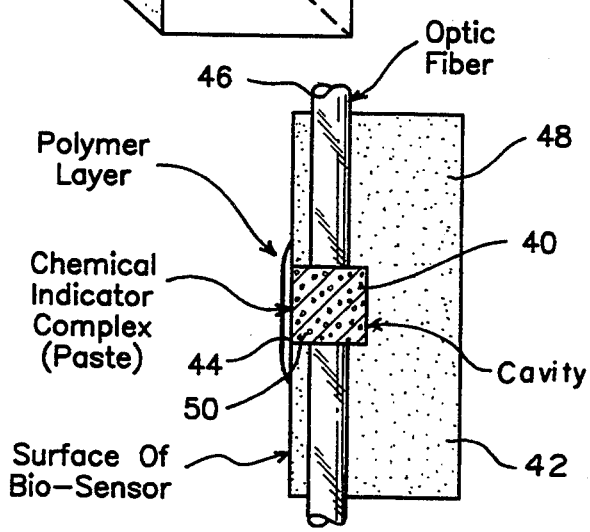
FIG. 3 is a side view in cross-section of the cavity of FIG. 2 with material in it.

Devices according to the present invention are useful with any thick material and any small cavity. With certain preferred embodiments such cavities have a volume of about five nanoliters or less. FIG. 2 illustrates one type of small cavity, a substantially cubic cavity 40 of a biosensor 42. This cavity 40 may be of microscopic size, e.g. with dimensions of about 100 microns (length, width, and depth); and therefore, an opening 44 into the cavity 40 is a square 100 microns on a side; of, e.g. a rectangular cavity of a length of about 100 microns and a depth and width of about 150 microns. Such a cavity holds about two nanoliters of thick material, e.g. a chemical indicator complex as described in co-pending co-owned application Ser. No. 07/810479 filed on Dec. 19, 1991 incorporated here for all purposes. FIG. 3 illustrates the cavity 40 which extends through a fiber optic 46 and into a body 48 of the biosensor 42. Thick material 50 (e.g. a chemical indicator complex) has been inserted into the cavity 40 with a device according to this invention filling the cavity. A polymer layer has been applied over the cavity opening 44.

Figure 4:
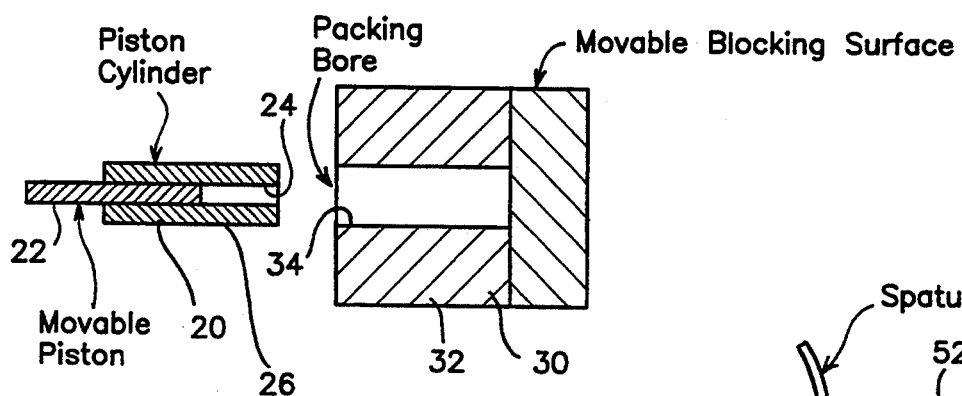
FIGS. 4–9 illustrate schematically and in cross-section a method and device according to the present invention.
Figure 5:
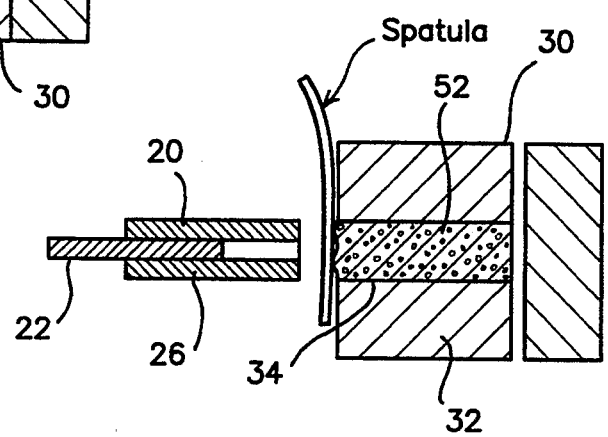
Figure 6:
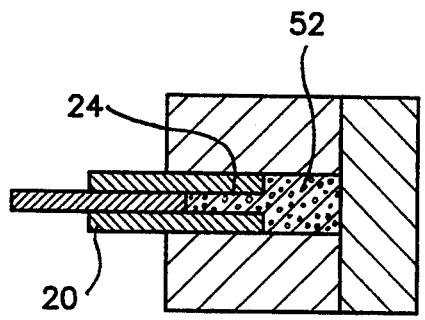
Figure 7:
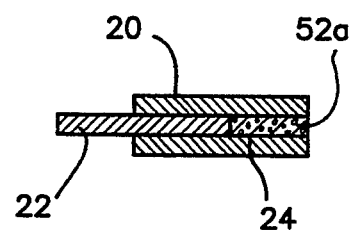

FIGS. 4-9 illustrate devices and methods according to the present invention. In FIG. 4 the piston/cylinder sub-assembly 20 is disposed apart from the containment sub-assembly 30. In FIG. 5 a desired amount of thick material 52 has been emplaced in the block bore 34 of the block 32. In FIG. 6, the piston/cylinder sub-assembly has been moved manually into the bore 34 and part of the thick material 52 has moved into the piston bore 24. As shown in FIG. 7, the piston 22 is positioned so that a known desired amount of the thick material 52a is held in the piston bore 24. Movement of the piston/cylinder sub-assembly into the block bore can be facilitated by using alignment means (not shown) such as a rib or rib on the outer surface of the cylinder and corresponding recesses on the interior of the block bore for receiving the ribs.

Figure 8:
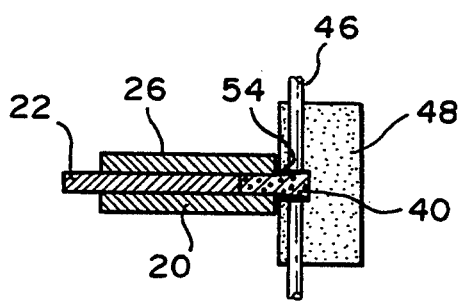
Figure 9:
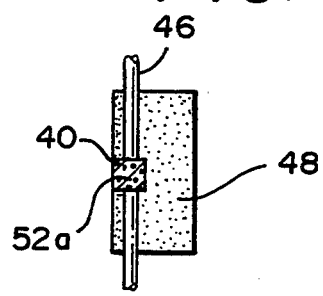

FIG. 8 shows the insertion of the material 52a into the cavity 40 by movement of the piston 22. An air path 54 is, preferably, maintained in the cavity 40 while the material moves into the cavity 40. FIG. 9 shows the thick material 52a within the cavity 40.

In one embodiment of a method according to this invention, the biosensor probe and filter optic having the cavity are transparent and, are held stationary in a vacuum chuck. The cylinder-piston is movably mounted in an X,Y,Z positioner. The opening of the cylinder-piston is moved in precise alignment with the cavity, and moved into contact therewith. The biosensor probe and the cylinder-piston are viewed under microscope at a magnification of fifty. The inside of the cavity is visible through the side wall. The thick material is a wet chemical indicating complex that is transparent and colored, and can be clearly seen entering the cavity. The quality of the fill can be visually validated. Trapped air is apparent, if it exists. Absence of entrapped air is validated by a uniform appearance of the wet material.

In certain embodiments wherein the piston bore is cylindrical, the slug of thick material emerging from the piston bore is also cylindrical and will maintain its shape until it reaches the bottom of a cavity and starts to spread transversely. Cavities which can be filled according to this invention include, but are not limited to:
- a cubic cavity with side dimensions equal to the slug diameter. Thus, the cylindrical slug contacts the four sides of the cubical cavity at four tangents, with unfilled space at the four corners. These spaces become filled as the slug flows transversely;
- a cavity which is cylindrical, but slightly larger (about 10% to 50% larger) than the slug diameter. Annular air space is filled (from the bottom up) as the slug flows transversely. For the above described cavities the cavity depth can be 150% of the width or diameter, or less.

Figure 10:
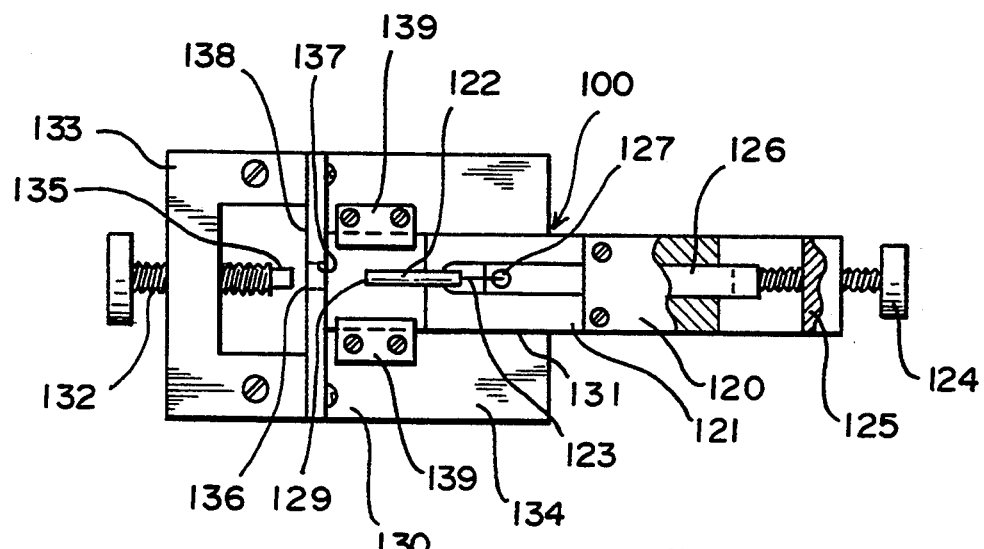
FIG. 10 is a top view of a device according to the present invention.
Figure 11:
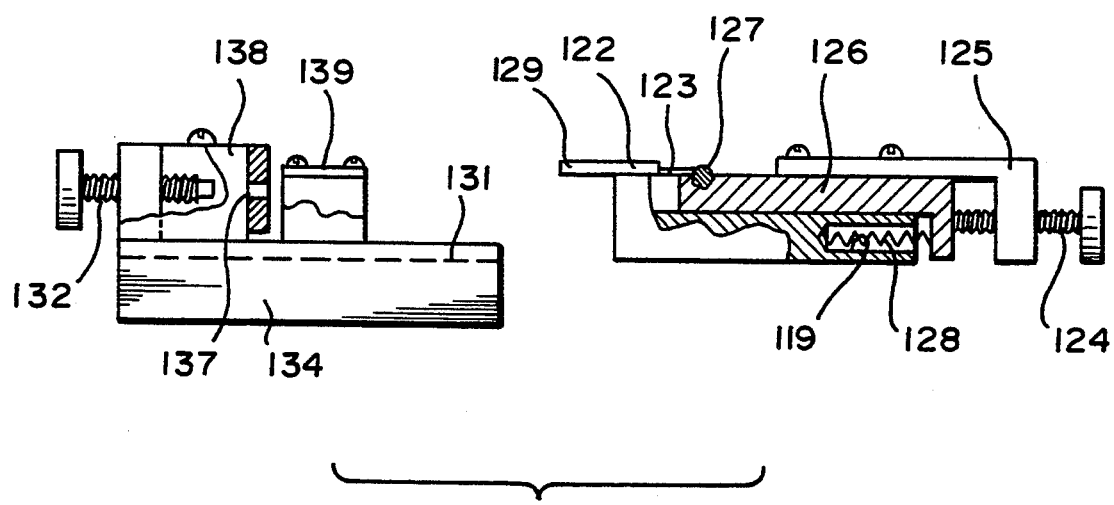
FIG. 11 is a side view of the device of FIG. 10.

FIGS. 10 and 11 illustrate a system 100 according to this invention which has a containment block sub-assembly 130 and a piston/cylinder sub-assembly 120. The piston/cylinder sub-assembly 120 has a base 121 which is received in a guide grove 131 of the sub-assembly 130. A threaded screw 132 extends through a wall 133 of a base 134 of the containment block sub-assembly 130. An end 135 of the screw 132 provides a movable blocking surface to block off an end 136 of a block bore 137 in a containment block 138. Braces 139 hold the base 121 in the guide groove 131.

A hollow cylinder tube 122 is secured to the piston base 121 and is disposed to enter the block bore 137 when the piston/cylinder sub-assembly is moved toward the containment block 138. Thixotropic material in the block bore 138 is thus transferred into a piston bore 129 of the cylinder tube 122. The interior volume of the cylinder tube 122 is changed as desired by withdrawing or further inserting a piston 123 (e.g. a piston wire as shown) by turning a screw 124 which is threaded through a bracket 125 which is secured to a slide member 126 to which the piston wire 123 is affixed, e.g. with potting material 127. A spring 128 interconnected between the piston base 121 and the slide member 126 is biased to push the slide member away from the containment block. The screw 124 opposes the force of the spring. This structure provides an anti-backlash and an anti-slack function for the slide member 126 and hence for the piston wire 123.

In conclusion, therefore, it is seen that the present invention and the embodiments disclosed herein and those covered by the appended claims are well adapted to carry out the objectives and obtain the ends set forth. Certain changes can be made in the described embodiments and in the claimed subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form its principles may be utilized.

What is claimed is:

1. In a system for installing an amount of a thick chemical indicator complex comprising liquid chemical indicating substance immobilized on solid particles in a microscopic cavity extending through a fiber optic in a biosensor, the cavity having a cavity volume, wherein the improvement comprising
   a block with a block bore therein for holding said thick chemical indicator complex,
   a material handling assembly having means for partially inserting said assembly into the block bore, the material handling assembly having a body with a body bore therethrough and a piston movably positioned in the body bore,
   the piston having means moving the piston for vacating a portion of the body bore so that upon insertion of the material handling assembly into the block bore an amount of the chemical indicator complex enters the vacated portion of the body bore, and
   the piston having means moving the piston for expelling the amount of the chemical indicator complex into the cavity at a pressure sufficiently low to prevent the liquid chemical indicating substance from separating from the solid particles.

2. The system of claim 1 wherein the microscopic cavity has a volume of five nanoliters or less.

3. The system of claim 1 wherein the microscopic cavity is cubic with a side about 100 microns long.

4. The system of claim 1 wherein the vacated portion of the body bore has a volume equivalent to the cavity volume.

5. The system of claim 1 wherein the block bore has a depth and the piston has a diameter, and the block bore's depth is equal to five times the piston's diameter or less.

6. The system of claim 1 wherein
the block is mounted on a block base having a guide groove therein, and
the material handling assembly has a base receivable in and movable in the guide groove.

7. The system of claim 6 wherein
the piston is secured to a slide member which is movably positioned in a slide bore in a base of the material handling assembly and
the slide member is movable to thereby move the piston in the body bore so that a desired portion of the body bore is vacated.

8. The system of claim 7 wherein
spring means is interconnected between the base of the material handling assembly and the slide member to push the slide member away from the block.

9. The system of claim 1 wherein a movable block surface is movably secured to the block and positioned for blocking an end of the block bore opposite an end of the block bore into which the body of the material handling assembly is inserted.

* * * * *